United States Patent
Koike et al.

(10) Patent No.: US 6,348,257 B1
(45) Date of Patent: Feb. 19, 2002

(54) ANTIBACTERIAL WATER ABSORBING COMPOSITION AND METHOD OF MANUFACTURE

(75) Inventors: Masanori Koike, Tokai; Masahisa Fujita, Kyoto; Kenji Tanaka, Otsu, all of (JP)

(73) Assignee: Sanyo Chemical Industries, Ltd., Kyoto (JP)

( * ) Notice: Subject to any disclaimer, the term of this patent is extended or adjusted under 35 U.S.C. 154(b) by 0 days.

(21) Appl. No.: 08/950,372

(22) Filed: Oct. 14, 1997

(30) Foreign Application Priority Data

Oct. 15, 1996 (JP) .............................................. 8-294461

(51) Int. Cl.$^7$ .................................................. B32B 3/00

(52) U.S. Cl. ....................................... 428/206; 428/220

(58) Field of Search ................................ 426/262, 654; 165/10 A; 252/70; 428/206, 220

(56) References Cited

FOREIGN PATENT DOCUMENTS

| | | |
|---|---|---|
| DE | 3036449 | 4/1981 |
| EP | 0122042 | 10/1984 |
| EP | 0606762 | 7/1994 |
| EP | 0641805 | 3/1995 |
| FR | 2331603 | 6/1977 |
| FR | 2669530 | 5/1992 |
| GB | 2084466 | 4/1982 |
| GB | 2263114 | 7/1993 |
| JP | 314867 | 2/1991 |
| JP | 417058 | 3/1992 |

*Primary Examiner*—Merrick Dixon
(74) *Attorney, Agent, or Firm*—Roylance, Abrams, Berdo & Goodman, L.L.P.

(57) ABSTRACT

An antibacterial water absorbing composition is provided which can suppress putrefaction by inhibiting the proliferation of fungus, microorganisms, etc. contained in urine, blood and body fluids, and can exhibits excellent water absorbing ability. The antibacterial water absorbing composition is prepared by mixing a water absorbing resin powder with a porous inorganic powder having absorbed therein an aqueous fluid of an antibacterial component.

21 Claims, No Drawings

ANTIBACTERIAL WATER ABSORBING COMPOSITION AND METHOD OF MANUFACTURE

BACKGROUND OF THE INVENTION

1. Field of the Invention

The present invention relates to an antibacterial water absorbing composition having excellent water absorption performance and antibacterial performance. The invention is further directed to absorbing materials particularly for absorbing urine, blood, other body fluids and the like, and to methods of producing the water absorbing composition.

2. Description of the Related Art

Water absorbing resins are widely used in water absorbing materials or water absorbing articles such as disposable diapers, incontinence pads, sanitary napkins, nursing pads, sheets for pets, absorbent materials for pets litter, excretion treating agents, waste blood gelling materials, drip absorbers and freshness retaining materials. The devices rely on the resins for their water absorbing performance, water retention capacities, gelling properties and the like. However, although the conventional water absorbing resin has excellent absorption and retention capacities for urine, blood and other body fluids, the resins do not have antibacterial properties.

Therefore, when the water absorbing resin absorbs urine, blood, and other body fluids and the like, the organic materials contained in the fluids absorbed by the resin are degraded by various fungus and microorganisms, thereby causing, for example, bad odors, skin irritations, and skin rashes. Further, the hydrogels are easily putrefied by the fungus and the microorganisms contained in the fluids being absorbed or the bacteria in the air, and bad odors may develop due to the putrefaction. To avoid these problems and to maintain a hygienic and safe environment, materials which exhibit both absorptive properties and antibacterial properties are desired. In particular, the problems of developing bad odors or rashes are serious in the water absorbing materials such as disposable diapers for the bedridden elderly and the sick. Accordingly, a continuing need exists to solve these problems.

The prior methods for providing absorbing materials with antibacterial properties include methods of spraying a water absorbing resin with an aqueous solution of specific antibacterial component as disclosed in Japanese Kokoku No. 3-14867. Other prior methods include adding an aqueous solution of a specific antibacterial component after mixing a water absorbing resin and an inorganic material together as disclosed in Japanese Kokoku No. 4-17058. The compositions prepared by these methods are proposed for use in water absorbing materials.

Although these prior compositions exhibit some antibacterial function and water absorbing function, they are not necessarily satisfactory for water absorbing materials. For example, in the method of spraying a water absorbing resin with an aqueous solution of a specific antibacterial component, the water absorbing resin easily coagulates and forms lumps when the resin contacts the aqueous solution of the antibacterial agent. Consequently, it is difficult to uniformly mix the water absorbing resin with the solution of an antibacterial component, and it is difficult to obtain a composition with the stabilized antibacterial properties. Furthermore, the spray process requires an evaporating step to remove the excess or other solvent after mixing and grinding and adjusting the particle size of the dried material, thereby complicating the production process.

The process of adding an aqueous solution of a specific antibacterial component to mixtures of a water absorbing resin and an inorganic material also forms lumps as described above, although usually not to the same extent. However, the aqueous solution of the antibacterial component is absorbed in the water absorbing resin and also in the inorganic material, so that the distribution of the antibacterial component becomes non-uniform. This causes large variations in the antibacterial performance of the composition and the material. Further, the increased likelihood of the dust escaping creates environmental concerns. The fine dust particles of the hydrophilic resins is difficult to control and remove from the air. Accordingly, there is a continuing need in the industry for improved methods of producing water absorbing resins with antibacterial properties.

SUMMARY OF THE INVENTION

The present invention is directed to antibacterial water absorbing compositions having excellent water absorption performance and antibacterial performance. The composition of the invention is a free-flowing powder having improved powder handling properties with lower amounts of dust being produced during manufacture. The composition is particularly useful for absorbing urine, blood, body fluids, and the like, and in the manufacture of absorbing materials such as disposable diapers, absorbent pads, sanitary napkins and the like.

The present invention is an antibacterial water absorbing composition comprising a mixture of powders of a water absorbing resin and an antibacterial powder mixture. The antibacterial powder mixture is prepared by allowing fine particles of porous inorganic adsorbent powders to adsorb an aqueous fluid of an antibacterial agent. The antibacterial water absorbing composition is obtained by allowing fine particles of porous inorganic powders to absorb an aqueous fluid of an antibacterial component and then mixing the particles with a particulate water absorbing resin.

Accordingly, a primary object of the invention is to provide an antibacterial water absorbing composition that is easy and economical to manufacture.

Another object of the invention is to provide an antibacterial water absorbing composition that is effective in inhibiting bacterial and fungal growth in aqueous fluids absorbed in the composition.

A further object of the invention is to provide an antibacterial water absorbing composition containing an antibacterial agent adsorbed in an inorganic porous adsorbent powder.

Still further object of the invention is to provide a method of producing an antibacterial water absorbing composition where the composition is produced by adsorbing an aqueous solution of an antibacterial agent in an inorganic porous adsorbent powder.

The objects of the invention are basically attained by providing an antibacterial water absorbing composition comprising a mixture of:

at least one particulate water absorbing resin;

and at least one antibacterial powders comprising at least one particulate inorganic adsorbent powder having adsorbed therein at least one antibacterial agent;

wherein said composition is a substantially free-flowing powder having water absorbing properties, and wherein said antibacterial agent inhibits bacterial growth in aqueous liquids adsorbed by said composition.

The objects of the invention are further attained by providing an antibacterial water absorbing material comprising at least one water absorbing substrate; and at least one water absorbent gel-forming composition, said composition comprising a mixture of a particulate water absorbing resin and an antibacterial powder comprising a particulate inorganic adsorbent powder having adsorbed therein an antibacterial agent.

The objects of the invention are also attained by providing a process for producing an antibacterial water absorbing composition comprising the step of:

mixing a particulate inorganic adsorbent and an aqueous fluid of an antibacterial agent whereby said antibacterial agent is adsorbed by said adsorbent to form an antibacterial powder, and mixing said antibacterial powder with a particulate water absorbing resin to produce said composition.

These and other objects, advantages and salient features of the invention will become apparent from the detailed description of the invention.

DETAILED DESCRIPTION OF THE INVENTION

The present invention is directed to a water absorbing composition having antibacterial properties. The composition contains an effective amount of an antibacterial agent to inhibit the growth of bacterial, fungus and other microorganisms in aqueous fluids absorbed in the composition. The invention is further directed to a method of producing the antibacterial water absorbing composition.

The antibacterial water absorbing composition basically comprises a substantially dry blend of a water absorbing resin and an antibacterial agent-containing powder. The antibacterial agent-containing powder comprises a particulate inorganic carrier and an antibacterial agent adsorbed in the carrier.

The antibacterial water absorbing composition contains about 0.1% to about 10% by weight of the antibacterial powder based on the weight of said water absorbent resin.

The carrier is a substantially dry, free-flowing particulate inorganic porous adsorbent. The adsorbent contains an effective amount of a compound having antibacterial and/or antifungal activity adsorbed on the adsorbent. The antibacterial composition is prepared by mixing an inorganic adsorbent with an aqueous fluid of an antibacterial agent. The aqueous fluid is provided in an amount which can be adsorbed by the adsorbent and produce a free-flowing powder.

The inorganic carrier is generally a particulate adsorbent having a porous form. Examples of suitable particulate inorganic porous adsorbent (A) for use in the present invention include natural or synthetic zeolites, silicon dioxide, aluminum oxide, magnesium oxide, and aluminum silicate and thereof. In embodiments of the invention, two or more of the adsorbents can be used in combination. Aluminum oxide, magnesium oxide, and silicon dioxide are generally preferred. Fine particulate hydrophilic silica prepared by wet process or dry process are most preferable.

The pore diameter of the inorganic particulate is not particularly limited so long as the adsorbent powders (A) are sufficiently porous to adsorb the antibacterial agent and release the antibacterial agent when the composition absorbs moisture. Typically, the inorganic particles have a pore diameter ranging from about 1 to 500 angstroms, and preferably from about 2 to about 200 angstroms.

The particle size of the inorganic porous adsorbent powder (A) is not particularly limited. The particles have an average particle size of primary particles typically within a range of about 0.01 to about 100 microns, preferably within a range of about 0.05 to about 50 microns, and more preferably within a range of about 0.05 to about 20 microns.

The specific surface area of the inorganic porous adsorbent powder (A) is not particularly limited. Typically, the surface area of the inorganic porous adsorbent powder (A) fall within a range of about 10 to about 800 $m^2/g$. Preferably, the inorganic porous adsorbent powder (A) have a surface area of about 20 to about 600 $m^2/g$ determined by the BET method.

Suitable examples said antibacterial agent (B) for use in the present invention include those which can suppress the proliferation of various fungus and bacterial, such as, for example, E. coli, Providencia vettgeri, Candida albicans, Staphylococcus and other microorganisms. The antibacterial agent is preferably water soluble.

Examples of suitable antibacterial agent (B) include quaternary ammonium salt compounds containing at least one aliphatic alkyl with 6 to 18 carbon atoms in its molecule, benzalkonium salt compounds, chlorohexidine compounds, polymethylenebisguanidine compounds, and mixtures thereof.

Examples of preferred quaternary ammonium salt compounds contain quaternary ammonium cation group with hydrochloride salt or organic acid salt, said cation group containing at least one aliphatic alkyl group having 6 to 18 carbon atoms. Examples of suitable quaternary ammonium groups include hexyl trimethyl ammonium, decyl trimethyl ammonium, lauryl trimethyl ammonium, myristyl trimethyl ammonium, cetyl trimethyl ammonium, stearyl trimethyl ammonium, didecyl dimethyl ammonium, dilauryl dimethyl ammonium, and distearyl dimethyl ammonium group. The anion can be from, for example, an inorganic compound such as hydrochloric acid, bromic acid, and nitric acid, and organic acid compounds such as aliphatic monocarboxylic acids having 1–30 carbon atoms, aliphatic oxycarboxylic acids, aliphatic polycarboxylic acids, and aromatic carboxylic acids.

Examples of benzalkonium compounds include benzalkonium chloride, benzalkonium gluconate, and benzalkonium adipate. The chlorohexidine compounds including, for example, chlorohexidine, chlorohexidine hydrochloride, and chlorohexidine gluconate. Examples of polymethylene bigu-anidine compounds include, hydrochlorides or gluconates of polyhexamethylene guanidine, and hydrochlorides or gluconates of polyoctamethylene guanidine.

The amount of the antibacterial agent (B) incorporated into the inorganic porous adsorbent powder (A) can vary depending on the effectiveness of the agent and the intended use of the resulting composition. The inorganic porous adsorbent powder (A) generally contains about 0.5% to about 40% by weight, and preferably about 1.0 to about 30% by weight of the antibacterial agent (B) based on the solid weight of the antibacterial powder (C). Thus, the ratio of the weight of the inorganic porous adsrobent powder (A) particles to the weight of the antibacterial agent (B) is about 60:40 to about 99. 5:0.5, and preferably about 70:30 to about 99:1.

The inorganic porous adsorbent powder (A) preferably includes at least 0.5% by weight of the antibacterial agent (B), since below this level the antibacterial activity is generally unacceptably low. To obtain the satisfactory antibacterial effect at lower % by weight of antibacterial agent, it is necessary to use a large volume of the antibacterial powder (C), which typically reduces the absorption performance of the resulting composition.

When the antibacterial powder (C) contains more than 40% by weight of the antibacterial agent (B), the adsorbency of the inorganic porous adsorbent powder (A) is insufficient, thereby deteriorating the powder flow properties. Furthermore, high amounts of the antibacterial agent require an additional drying process to improve the powder flow properties, thereby increasing the manufacturing costs.

The antibacterial agent (B) is preferably prepared as an aqueous fluid, such as an aqueous solution, dispersion or emulsion more preferably aqueous solution. The aqueous fluid is then mixed with the inorganic porous adsorbent powder (A). The aqueous fluid is adsorbed by the inorganic particulate adsorbent to form a free-flowing powder or pulverulent material. The resulting powder can be dried as necessary to remove excess moisture. The amount of the aqueous fluid of the antibacterial agent (B) mixed with the inorganic particulate adsorbent (A) will vary depending on the selection of adsorbent (A), the concentration of fluid of agent (B) and the expected use of the final product. The antibacterial agent (B) typically is mixed with about 0.7% to about 70% by weight, and preferably about 1.0% to 60% by weight of the aqueous fluid based on the combined weight of the inorganic adsorbent (A) and aqueous fluid. The resulting mixture has an adsorbent (A) to aqueous fluid ratio of about 30:70 to about 99.3:0.7, and preferably about 40:60 to about 99:1.

When the inorganic adsorbent contains less than about 0.7% of the aqueous fluid of the antibacterial agent (B), the concentration of the antibacterial agent (B) in the aqueous fluid is required to be so high that it is difficult to homogeneously disperse the antibacterial agent in the aqueous fluid. Mixing the inorganic adsorbent (A) with more than 70% by weight of the aqueous fluid produces a powder with poor flow properties. Additionally drying and grinding steps are then required in order to improve the powder flow properties, which increase the cost of manufacture.

The average particle size of the antibacterial powder (C) ranges from about 0.1 to about 100 microns, and preferably ranges from about 0.5 to about 50 microns. An average particle size less than 0.1 microns results in an increase of dusting during handling. An average particle size greater than about 100 microns is difficult to mix homogeneously with the water absorbing resin (D).

The antibacterial water absorbing composition of the present invention can be prepared using standard industrial apparatus capable of mixing the inorganic particulate adsorbent (A) and the aqueous fluid of the antibacterial agent (B) to allow the adsorbent (A) to absorb the aqueous fluid.

Examples of suitable apparatus include a V-shaped rotating mixer, a Nauta blender, a ribbon blender, a planetary mixer, a conical blender, a turbulizer, an universal mixer, a kneader, and a screw mixer as known in the art.

The antibacterial powder (C) can be prepared by adding the adsorbent (A) to a mixer and adding an aqueous fluid of an antibacterial agent (B) in incremental amounts to uniformly disperse the materials. Typically, the aqueous fluid is added by spraying at a controlled rate while operating the mixer. In further embodiments, the aqueous fluid can be added in a batch process.

The inorganic adsorbent (A) and the aqueous fluid of the antibacterial agent (B) can be mixed at room temperature or at elevated temperatures. Typically, the components are mixed for about 10 to 60 minutes or until thoroughly mixed and the aqueous fluid is adsorbed.

The water absorbing resin (D) is preferably a water absorbing resin containing a carboxyl or carboxylate group (salt of carboxyl group) as the constituent unit. The resin can be produced according to known processes for producing water absorbing resins.

Examples of preferred water absorbing resin (D) for use in the present invention include:

crosslinked copolymers of starch-acrylic acid or acrylates as disclosed in Japanese Kokoku Nos. 53-46199, 53-46200;

self-crosslinked polyacrylates and salts thereof or crosslinked polyacrylates and salts thereof obtained by reversed-phase suspension polymerization, as disclosed in Japanese Kokoku No. 54-30710 and Kokai No. 56-26909;

crosslinked polyacrylic acids and salts thereof obtained by aqueous solution polymerization such as, for example, adiabatic polymerization, thin-film polymerization, and spray polymerization, as disclosed in Japanese Kokai No. 55-133413;

saponificated copolymers of vinyl esters and unsaturated carboxylic acids or the derivatives thereof, as disclosed in Japanese Kokai Nos. 52-14689 and 52-27455;

crosslinked polyacrylic acids and salts thereof prepared by copolymerization of a monomer containing a sulfonic acid group or sulfonate group (salt of sulfonic acid group) as disclosed in Japanese Kokai Nos. 58-2312 and 61-36309; and crosslinked copolymers of isobutylene-maleic acid anhydrides, hydrolyzates of crosslinked copolymers of starch-acrylonitrile, crosslinked carboxymethylcellulose derivatives, and crosslinked copolymers of acrylic acid or acrylate-acrylami des.

Two or more of these water absorbing resins may be used in combination. The surface-crosslinked water absorbing resins which are crosslinked on the surface with a crosslinking agent are also preferable for use in the present invention.

The salts of the monomers normally refer to a sodium salt and/or a potassium salt, but may be a salt of an organic acid such as an ammonium salt or an amine salt depending on the application of the polymerization process.

The water insoluble water absorbing resin containing a carboxylic group and a carboxylate group as the principal constituent units are most preferable since these polymers exhibit relatively larger water absorption capacity.

The water insoluble water absorbing resin containing a carboxylic group as the constituent unit have about 20–50 mole %, and preferably about 25–45 mole % of the carboxylic component based on the total number of the carboxylic and carboxylate groups. The carboxylic groups of a carboxylic component are able to adsorb ammonia.

The water absorption performance of the resin is reduced when the molar amount of the carboxylic component based on the total amount of the carboxylic and carboxylate components exceed 50 mole %. In addition, the pH of the resultant antibacterial water absorbing composition falls in the acidic range. The acidic water absorbing resin is undesirable when the resin is used in devices which contact to the skin since skin irritation usually occurs.

A carboxylic component content of less than 20 mole % results in poor ammonia adsorption. In addition, the pH of the resultant antibacterial water absorbing agent composition becomes alkaline, which also has a possibility to cause skin irritation.

The absorbency of the water absorbing resin (D) for a saline solution (an aqueous solution of 0.9% sodium chloride) is typically about 30 g/g or more, preferably 35 to 80 g/g, and more preferably 40 to 75 g/g. The absorbency is measured by using a method described below.

The shape of the water absorbing resin (D) is not particularly limited so long as it is in powdered form. The examples of suitable shapes include grainy shapes, granular shapes, agglomerated shapes, scaly shapes, lumpy shapes, pearly shapes, and impalpable powdered shapes.

The particle size distribution of the water absorbing resin (D) is also not particularly limited. Typically, the diameter of 90 wt % or more of the particles is about 1 mm or less. Preferably, the diameter of about 90 wt % or more of the particles is from about 0.1 to about 0.9 mm.

The water absorbing resin (D) and the inorganic powder mixture (C) can be mixed at a room temperature, or under heated conditions as required using standard apparatus as described above. Typically, the components are mixed for about 10 to 60 minutes. Other methods of preparation of the antibacterial water absorbing composition will become apparent to one of ordinary skill in the art.

The preparation of the antibacterial absorbing composition and mixing of the inorganic adsorbent (A) and aqueous fluid of the antibacterial agent (B) can be carried out in separate apparatuses, or in the same apparatus. Alternatively, the antibacterial absorbing composition can be line-blended in a powder transportation line during the process for producing the water absorbing resin (D).

The shape and the particle size distribution of the resulting antibacterial water absorbing composition of the present invention is not particularly limited. Suitable shapes include grainy shapes, granular shapes, agglomerate shapes, scaly shapes, lumpy shapes, pearly shapes and impalpable powdered shapes.

The particle size distribution of the resulting antibacterial water absorbing composition typically have about 90 wt % or more of the particles with a diameter of about 0.05 to 1 mm. Preferably, about 90 wt % or more of the particles have a particle diameter of about 0.1 to about 0.8 mm.

The antibacterial water absorbing composition of the present invention can be combined with other additives. Examples of suitable additives include organic powders as a bulk filler or an additive such as pulp powders, cellulose derivatives, and natural polysaccharides, inorganic powders such as calcium carbonate, bentonite, and activated carbon, antioxidants, surfactants, deodorants, coloring agents, and perfumes. The additives are usually combined with the antibacterial water absorbing composition in the amount of about 10 wt % or less based on the combined weight of the additives and the antibacterial water absorbing composition.

The antibacterial water absorbing composition of the present invention is satisfactory in both absorption and antibacterial effects when contacted with aqueous fluids. The antibacterial water absorbing composition can be used for water absorbing material in any method in which the antibacterial water absorbing composition is retained in a suitable water absorbing substrate which is used as support. The examples of the method of producing water absorbing material include scattering the antibacterial water absorbing composition between two layers of pulps or other heat fusible fibrous materials and fusing, if necessary, the layers together, mixing the antibacterial water absorbing composition with a pulp or other heat fusible fibrous materials and fusing, if necessary, the fibers together, and sandwiching the antibacterial water absorbing composition between two or more water absorbent papers, tissue paper, non-woven fibrous sheets, or fabric sheets and bonding the layers together.

The amount of the antibacterial water absorbing composition combined with the water absorbing substrate can vary depending on the kind and the size of absorbing substrate, and the desired absorbing performance. For example, in the case of disposable diapers and incontinence pads, the amount of the antibacterial water absorbent composition is typically from 3 to 25 g/piece. Alternatively, for sanitary napkins, panty liners, and nursing pads, the amount of the antibacterial water absorbent composition is typically from 0.2 to 5 g/piece. Further, when sandwiched between two or more of water absorbent papers or non-woven fabrics, the amount of the antibacterial water absorbent composition is typically from 10 to 80 g/m$^2$.

EXAMPLES

The present invention will be more specifically described with respect to the following examples and comparative examples. However, it should be understood that the present invention is not limited thereto. The absorbency and the antibacterial effect of the antibacterial water absorbing composition, and the evaluation of the water absorbent materials employing the antibacterial water absorbing composition were measured with the following methods. All percentages are based on weight unless otherwise indicated.

1. Absorbency

A tea bag of 250-mesh nylon net is charged with 1 g of a sample antibacterial water absorbing composition, immersed in excess physiological saline solution (0.9% NaCl aqueous solution) for 1 hour to absorb the solution. The bag is removed from the saline solution and drained by hanging for 15 minutes. The weight gain of the composition is measured. The weight gain is defined as the absorbency.

2. Antibacterial Test for the Antibacterial Water Absorbing Composition 3.45 g of sensitive broth medium and 150 ml of water are charged into a 200 ml beaker and dissolved, followed by autoclave sterilization. 1 g of test sample antibacterial water absorbing composition is added in the culture medium, then allowed to swell while stirring continuously.

5 ml of the culture medium containing the test sample composition are placed in a culture dish. A culture sample containing $E.$ $coli$ is inoculated onto the medium at a cell count of $1 \times 10^6$ piece/ml.

The viable cell counts are measured after 2 hours and 10 hours, respectively. The cell count is measured by counting the number of colonies in accordance with a plate culture method after a stepwise dilution.

The result of the blank test sample, in which $E.$ $coli$ is inoculated onto the culture medium without the test sample composition, showed that the viable cell count was $5 \times 10^8$ number/ml after 2 hours, and $9 \times 10^9$ number/ml after 10 hours.

3. Evaluation of the Water Absorptive Materials Employing the Antibacterial Water Absorbing Composition Preparation of the Absorbent Material A polyethylene sheet cut into a rectangular shape of 14 cm by 35 cm is overlapped with a tissue paper and a fluff pulp of 100 g/m$^2$ of the same size.

10 g of the sample composition are then uniformly scattered over the fluff pulp layer followed by another pulp layer having a unit distribution of 50 g/m$^2$. A layer of tissue paper and a non-woven fabric are then placed over the pulp layer. A model diaper is made by laminating the layers by pressing the layers of material together at a pressure of 5 Kg/cm$^2$ for 90 seconds.

Test for Odor Suppression 80 ml of fresh human urine is added to the central part of the absorbing material which include the antibacterial water absorbing composition. The absorbing material is placed in a 5-liter wide-mounted bottle, sealed, and stored in a thermostatic chamber at 40° C. for 10 hours.

The bottle is then opened in an odorless room, and the odor generation is measured in accordance with the following 6-step evaluation. 10 panelers who are qualified for odor detecting ability according to T&T olfactometer method evaluate the odor level, and the average is taken.

0: odorless
1: barely sensible odor (sensible concentration)
2: recognizable faint odor (recognizable concentration)
3: easily recognizable odor
4: strong odor
5: irritating odor 4. Test for the Performance of the Absorbing Material
Absorption The absorbing material is immersed in excess physiological saline solution for 30 minutes, followed by placing on a wire netting, and drained by placing 10kg of weight for 20 minutes. The weight gain was then measured and the weight gain is defined as the absorption.

Re-wet Amount 50 ml of synthetic urine are poured into the central part of the model diaper. After 10 minutes, 10 pieces of filter paper measuring 10 cm by 10 cm are stacked on the central part of the diaper, and a 3.5 Kg weight is placed on the filter papers. The weight gain of the filter paper after 3 minutes is measured, and is defined to be re-wet amount. The smaller re-wet amount provides an improved dry feeling of the surface of the absorbing material.

Example 1

76.6 g of sodium acrylate, 23 g of acrylic acid, 0.4 g of N,N'-methylenebisacrylamide, and 295 g of deionized water were charged into a one-liter glass reactor. The contents were stirred and mixed while the temperature of the contents was kept at 5° C.

After the dissolved oxygen content was reduced to 1 ppm or less by flowing nitrogen gas into the contents, 1 g of 1% aqueous solution of hydrogen peroxide, 1.2 g of 0.2% aqueous solution of ascorbic acid, and 2.4 g of 2% aqueous solution of 2,2'-azobisaminodipropanedihydrochloride were added and polymerized for about 5 hours to obtain a hydrogel polymer containing 25% water absorbing resin.

The hydrogel polymer was dried under reduced pressure at 90° C., and ground with a pin mill. The particle size was then adjusted so that about 95% by weight of the water absorbing resin had a particle size of about 850–150 microns. The absorbency of the resin powder was 58 g/g.

50 g of porous inorganic powders consisting of a mixture of aluminum oxide and silicon oxide (sold under the tradename KYOWAAD 700, from Kyowa Kagaku, Japan) were charged into a 300 ml beaker. 50 g of an aqueous solution of cetyltrimethylammonium chloride (sold under the tradename LEBON TM-16, from Sanyo Chemical Industries, Japan; 30% aqueous solution) was gradually added while stirring with a glass rod to obtain the homogenous inorganic powder mixture. The average particle size of the inorganic powder mixture was about 40 microns.

100 g of the water absorbing resin powder and 5.4 g of the inorganic powder mixture were charged in another 300 ml beaker, and homogeneously mixed while stirring with a glass rod to obtain the antibacterial water absorbing composition. The results of measuring the absorbency and the antibacterial effect of the antibacterial water absorbing composition of Example 1 are shown in Table 1.

Example 2

An antibacterial water absorbing composition was obtained in the same manner as in Example 1 except using a powder mixture prepared from porous silica available under the tradename CARPLEX #80-D from Sionogi Seiyaku, Japan, instead of the aluminum oxide and silicon oxide porous inorganic powders of Example 1.

The results of measuring the absorbency and the antibacterial effect of the antibacterial water absorbing composition of Example 2 are shown in Table 1. The average particle size of the powder mixture was 50 microns.

Example 3

An antibacterial water absorbing composition was obtained in the same manner as in Example 1 except using a powder mixture from a 30% aqueous solution of didecyldimethylammonium of gluconate instead of a powder mixture from a 30% aqueous solution of cetyltrimethylammonium chloride.

The results of measuring the absorbency and the antibacterial effect of the antibacterial water absorbing composition of Example 3 are shown in Table 1.

Example 4

An antibacterial water absorbing composition was obtained in the same manner as in Example 1 except using the commercially available water absorbing resin available under the tradename SANWET IM-1000 from Sanyo Chemical Industries, Japan, which is a crosslinked copolymer of starch-sodium acrylate having a neutralized degree of 70 mole %. The results of measuring the absorbency and the antibacterial effect of the antibacterial water absorbing composition of Example 4 are shown in Table 1.

Example 5

An antibacterial water absorbing composition was obtained in the same manner as in Example 1 except using the commercially available water absorbing resin available under the tradename SANWET IM-5800 from Sanyo Chemical Industries, Japan, which is a surface-crosslinked water absorbing resin of crosslinked sodium polyacrylate having a neutralized degree of 70 mole %. The results of measuring the absorbency and the antibacterial effect of the antibacterial water absorbing composition of Example 5 are shown in Table 1.

Examples 6 and 7

Two antibacterial water absorbing compositions were obtained in the same manner as in Example 1 except respectively using 75 g (Example 6) and 25 g (Example 7) of 30% aqueous solutions of cetyltrimethylammonium chloride. The results of measuring the absorbency and the antibacterial effects of the antibacterial water absorbing composition of Example 6 and the antibacterial water absorbing composition of Example 7 are respectively shown in Table 1.

Examples 8–14

The antibacterial water absorbing compositions prepared in Examples 1–7 were applied at a unit distribution of 60 g/m$^2$ between two layers of pulp having unit distribution of each 100 g/m$^2$, followed by uniform compression at a pressure of 5 Kg/M$^2$. Each of the resultant laminates was further provided with a polyethylene film at its lower lamination side and a non-woven fabric mainly composed of a polypropylene fiber at its upper lamination side, and cut to a width of 14 cm and length of 35 cm to prepare the absorbing materials of Examples 8–14. The results of measuring the performances of these absorbing materials are shown in Table 2.

Comparative Example 1

The absorbency and antibacterial properties were determined for the water absorbing resin powder prepared in Example 1 before mixing with the inorganic powder. The results are shown in Table 1.

Comparative Examples 2 and 3

The absorbency and antibacterial properties were determined for the SANWET IM-1000 and SANWET IM-5800, respectively. The results are shown in Table 1.

Comparative Example 4

100 g of the water absorbing resin powder prepared in Example 1 were charged in a 300 ml beaker. 2.7 g of a 30% aqueous solution of cetyltrimethylammonium chloride were sprayed into the beaker while stirring with a glass rod. The resultant product produced lumps where the water absorbing resin powders coagulated with each other. The lumps were dried and coarsely ground to obtain a comparative antibacterial water absorbing composition.

The results of measuring the absorbency and the antibacterial effect of the comparative antibacterial water absorbing composition of Comparative Example 4 are shown in Table 1.

Comparative Example 5

100 g of the water absorbing resin powder prepared in Example 1 were charged in a 300 ml beaker. 2.7 g of porous inorganic powders consisting of a mixture of aluminum oxide and silicon oxide available under the tradename KYOWAAD 700 from Kyowa Kagaku, Japan, were added and mixed while stirring with a glass rod.

To this mixture, 2.7 g of a 30% aqueous solution of cetyltrimethylammonium chloride was gradually added while stirring with a glass rod to obtain a comparative antibacterial water absorbing composition.

The results of measuring the absorbency and the antibacterial effect of the antibacterial water absorbing agent composition of Comparative Example 5 are shown in Table 1. The dust rising in this antibacterial water absorbing composition was considerably higher compared to the antibacterial water absorbing compositions of Examples 1–7.

Comparative Examples 6–10

In the same manner as in Examples 8–14, the water absorbing resin powder of Comparative Example 1, the commercially available water absorbing resins of Comparative Examples 2 and 3, the comparative antibacterial water absorbing compositions of Comparative Example 4 and Comparative Example 5 were used to produce water absorbent materials of Comparative Examples 6–10. The results of measuring the performances of these absorbent materials of Comparative Examples 6–10 are shown in Table 2.

TABLE 1

|  | Absorbency (g/g) | Antibacterial Test (Colonies number/ml) | |
| --- | --- | --- | --- |
|  |  | After 2 hours | After 10 hours |
| Example |  |  |  |
| 1 | 59 | $2.2 \times 10^2$ | $4.4 \times 10^2$ |
| 2 | 61 | $1.8 \times 10^2$ | $4.1 \times 10^2$ |
| 3 | 60 | $2.3 \times 10$ | $1.2 \times 10$ |
| 4 | 62 | $3.2 \times 10^2$ | $4.9 \times 10^2$ |
| 5 | 57 | $2.0 \times 10^2$ | $3.2 \times 10^2$ |
| 6 | 56 | $2.3 \times 10$ | $1.1 \times 10^2$ |
| 7 | 60 | $5.5 \times 10^2$ | $3.9 \times 10^2$ |
| Comparative Example |  |  |  |
| 1 | 58 | $3.2 \times 10^8$ | $4.1 \times 10^9$ |
| 2 | 63 | $4.8 \times 10^8$ | $5.4 \times 10^9$ |
| 3 | 60 | $2.1 \times 10^8$ | $3.0 \times 10^9$ |
| 4 | 53 | $7.1 \times 10^3$ | $8.0 \times 10^5$ |
| 5 | 56 | $1.8 \times 10^3$ | $3.2 \times 10^4$ |

TABLE 2

|  | Absorption (g/piece) | Re-wet amount (g) | Test for Bad Odor Suppression |
| --- | --- | --- | --- |
| Example |  |  |  |
| 8 | 480 | 0.3 | 1.2 |
| 9 | 485 | 0.2 | 1.2 |
| 10 | 485 | 0.2 | 0.9 |
| 11 | 490 | 0.3 | 1.3 |
| 12 | 470 | 0.1 | 1.2 |
| 13 | 475 | 0.5 | 1.0 |
| 14 | 485 | 0.3 | 1.6 |
| Comparative Example |  |  |  |
| 6 | 490 | 0.4 | 4.4 |
| 7 | 485 | 0.5 | 4.6 |
| 8 | 475 | 0.4 | 4.1 |
| 9 | 450 | 1.6 | 3.2 |
| 10 | 470 | 1.1 | 2.8 |

The antibacterial water absorbing composition of the present invention has several advantages and desirable effects. The composition exhibits the excellent antibacterial effects in addition to the absorption performance. The antibacterial component suppresses degradation and putrefaction by fungus, microorganisms, and bacteria of the organic materials contained in urine, blood, and body fluids, and the like, absorbed in the water absorbing resin. Generation of foul odors are inhibited by the suppression of the putrefaction. The handling properties of the water absorbing compositions are improved as a result of low dust formation and good anti-caking property. Absorbing materials can be obtained by the same methods as in the conventional water absorbing resins.

Disposable diapers and sanitary napkins made using the water absorbing materials have antibacterial activity, thereby suppressing foul odors, or skin irritations and rashes. The antibacterial water absorbing composition of the present invention is especially useful for various water absorbing materials including disposable diapers for adults and infants, incontinence pads, sanitary napkins, panty liners, mother breast pads, nursing pads, after-parturition mats, and medical under pads.

Further, the composition of the present invention is useful for an excretion treating agent and as a gellation of various body fluids such as pet urine and waste blood to prevent the development of foul odors. The composition is also useful in the production of sheets or tapes of water absorptive materials such as a pet sheet or a drip absorber. Further, the present invention is useful for the application employing gels prepared by allowing water absorbing resins to absorb water (e.g., coldness retaining materials, artificial snow, and water beds), and the application involving bad odor development due to putrefaction such as sludge solidification agents and anti-mildewing agents for walls.

Various details of the invention may be changed without departing from its spirit nor its scope. Furthermore, the foregoing description of the embodiments according to the present invention is provided for the purpose of illustration only, and not for the purpose of limiting the invention as defined by the appended claims and their equivalents.

What is claimed is:

1. An antibacterial water absorbing composition comprising a mixture of:
    at least one particulate water absorbing resin; and
    at least one antibacterial powder comprising at least one particulate inorganic adsorbent having adsorbed therein at least one antibacterial agent;
    wherein said composition is a substantially free-flowing powder having water absorbing properties, and wherein said antibacterial agent decreases bacterial growth in aqueous liquids absorbed by said composition.

2. The composition of claim 1, wherein said antibacterial powder comprises about 0.5 to about 40% by weight of said antibacterial agent and about 60% to 99.5% by weight of said particulate inorganic adsorbent.

3. The composition of claim 1, wherein said composition comprises about 0.1 to about 10 parts by weight of said antibacterial powder based on 100 parts of said particulate water absorbing resin.

4. The composition of claim 1, wherein said antibacterial powder has an average particle size of about 0.1 to about 100 microns.

5. The composition of claim 1, wherein said antibacterial agent is selected from the group consisting of $C_{6-18}$ aliphatic alkyl quaternary ammonium salt compounds, benzalkonium salt compounds, chlorohexidine compounds and polymethylenebiguanidine compounds.

6. The composition of claim 1, wherein about 90% by weight of said particulate water absorbing resin has a particle size of about 0.1 mm to about 0.9 mm.

7. The composition of claim 1, wherein said water absorbing resin has an absorbency of at least 30 g/g, calculated from absorbency of 0.9% saline solution.

8. The composition of claim 1, wherein said inorganic adsorbent is selected from the group consisting of zeolite, aluminum oxide, magnesium oxide, silicon dioxide, aluminum silicate, and mixtures thereof.

9. An antibacterial water absorbing material comprising:
    at least one water absorbing substrate; and
    at least one antibacterial water absorbing composition, said composition comprising a mixture of a particulate water absorbing resin and an antibacterial powder comprising at least one particulate inorganic adsorbent having adsorbed therein at least one antibacterial agent.

10. The antibacterial water absorbing material of claim 9, wherein said substrate is a paper or non-woven fibrous sheet.

11. The antibacterial water absorbing material of claim 9, further comprising at least two of said water absorbing substrates, and wherein said antibacterial water absorbing composition is disposed between said substrates.

12. The antibacterial water absorbing material of claim 9, wherein said antibacterial powder comprises about 0.5 to about 40% by weight of said antibacterial agent and about 60% to 99.5% by weight of said particulate inorganic absorbent.

13. The antibacterial water absorbent material of claim 9, wherein said water absorbent gel-forming composition comprises about 0.1 to about 10 parts by weight of said antibacterial powder based on 100 parts of said water absorbing resin.

14. The antibacterial water absorbent material of claim 9, wherein said antibacterial powder has an average particle size of about 0.1 to about 100 microns.

15. The antibacterial water absorbent material of claim 9, wherein said antibacterial agent is selected from the group consisting of $C_{6-18}$ aliphatic alkyl quaternary ammonium salt compounds, benzalkonium salt compounds, chlorohexidine compounds and polymethylenebiguanidine compounds.

16. The antibacterial water absorbent material of claim 9, wherein about 90% by weight of said particulate water absorbing resin has a particle size of about 0.1 mm to about 0.9 mm.

17. The antibacterial water absorbent material of claim 9, wherein said inorganic adsorbent is selected from the group consisting of zeolite, aluminum oxide, magnesium oxide, silicon dioxide, aluminum silicate, and mixtures thereof.

18. A process for producing an antibacterial water absorbing composition comprising the steps of:
    mixing a particulate inorganic adsorbent and an aqueous fluid containing an antibacterial agent whereby said antibacterial agent is adsorbed by said adsorbent to form an antibacterial powder, and
    mixing said antibacterial powder with a particulate water absorbing resin to produce said composition.

19. The process of claim 18, wherein said aqueous fluid is selected from the group consisting of aqueous solutions, aqueous emulsions and aqueous dispersions.

20. The process of claim 18, wherein said inorganic adsorbent contains about 0.5% to about 40.0% by weight of said antibacterial agent and about 60% to 99.5% by weight of said particulate inorganic adsorbents on the weight of the antibacterial powder.

21. The process of claim 18, comprising mixing about 0.1 to about 10 parts by weight of said antibacterial powder based on total weight of said composition with said water absorbing resin.

* * * * *